United States Patent
Bakker et al.

(10) Patent No.: US 7,750,331 B2
(45) Date of Patent: Jul. 6, 2010

(54) METHOD AND DEVICE FOR IMAGING AN INTERIOR OF A TURBID MEDIUM USING AN AMPLIFICATION FACTOR SELECTED FROM AN ESTIMATE OF EXPECTED ELECTRICAL SIGNAL STRENGTH

(75) Inventors: Levinus Pieter Bakker, Eindhoven (NL); Gert 'T Hooft, Eindhoven (NL); Martinus Bernardus Van Der Mark, Eindhoven (NL); Michael Cornelis Van Beek, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/094,634

(22) PCT Filed: Nov. 21, 2006

(86) PCT No.: PCT/IB2006/054349

§ 371 (c)(1),
(2), (4) Date: May 22, 2008

(87) PCT Pub. No.: WO2007/060602

PCT Pub. Date: May 31, 2007

(65) Prior Publication Data

US 2008/0290256 A1    Nov. 27, 2008

(30) Foreign Application Priority Data

Nov. 23, 2005 (EP) .................................. 05111161

(51) Int. Cl.
*G01N 15/06* (2006.01)
*G01N 21/49* (2006.01)
*G01N 21/85* (2006.01)

(52) U.S. Cl. ............ 250/573; 250/214 A; 250/214 AG; 356/432; 600/476

(58) Field of Classification Search ................. 250/573, 250/214 R, 214.1, 214 A, 214 AG; 356/432, 356/440, 344; 600/476; 330/254, 278
See application file for complete search history.

(56) References Cited

U.S. PATENT DOCUMENTS 6,331,700 B1    12/2001   Wake et al.

(Continued)

FOREIGN PATENT DOCUMENTS

| EP | 1338239 A2 | 8/2003 |
|---|---|---|
| WO | WO9220273 | 11/1992 |

OTHER PUBLICATIONS

Nissila et al: "Instrumentation and Calibration Methods for the Multichannel Measurement of Phase and Amplitude in Optical Tomography"; Review of Scientific Instruments 76, 2005, pp. 044302-1-044302-10.

*Primary Examiner*—Thanh X Luu
*Assistant Examiner*—Francis M LeGasse, Jr.

(57) ABSTRACT

The invention relates to a method and device (1) for imaging an interior of a turbid medium (55). A turbid medium (55) inside a measurement volume (15) is irradiated from a plurality of source positions (25*a*) with light from a light source (5), and light emanating from the measurement volume (15) is detected from a plurality of detection positions (25*b*). An image of the interior of the turbid medium (55) is reconstructed from the detected light. In both the method and the device (1), detector signals can be amplified for each source position-detection position pair by a multi-gain amplification unit comprising an amplifier circuit (60). The amplification factor is selected from a number of possible amplification factors based on detected signal strength in the prior art. According to the invention, however, the method and device are adapted such that the amplification factor is selected for at least one source position-detection position pair on the basis of an estimate of expected electrical signal strength.

20 Claims, 3 Drawing Sheets

U.S. PATENT DOCUMENTS

| | | |
|---|---|---|
| 6,339,216 B1 | 1/2002 | Wake |
| 6,480,281 B1 * | 11/2002 | Van Der Mark et al. ..... 356/432 |
| 6,681,130 B2 | 1/2004 | Wake et al. |
| 2002/0100864 A1 * | 8/2002 | Wake ...................... 250/208.1 |
| 2003/0228151 A1 * | 12/2003 | Niiho et al. ................. 398/115 |
| 2005/0136872 A1 * | 6/2005 | Yoshizawa et al. ....... 455/232.1 |
| 2005/0197583 A1 | 9/2005 | Chance |

* cited by examiner

METHOD AND DEVICE FOR IMAGING AN INTERIOR OF A TURBID MEDIUM USING AN AMPLIFICATION FACTOR SELECTED FROM AN ESTIMATE OF EXPECTED ELECTRICAL SIGNAL STRENGTH

The invention relates to a method of imaging an interior of a turbid medium, comprising the following steps:

a) accommodation of the turbid medium inside a measurement volume;

b) irradiation of the turbid medium with light from a light source from a plurality of source positions relative to the turbid medium;

c) acquisition of detector signals by detection of light emanating from the measurement volume from a plurality of detection positions as a result of said irradiation of the turbid medium;

d) amplification of the detector signals for each source position-detection position pair using multi-gain amplification units, with each unit being set to a selected amplification factor.

The invention also relates to a device for imaging an interior of a turbid medium comprising:

a) a measurement volume for accommodating the turbid medium;

b) a light source for irradiating the turbid medium from a plurality of source positions relative to the turbid medium;

c) a photodetector unit for acquisition of detector signals by detecting light emanating from the measurement volume from a plurality of detection positions as a result of said irradiation of the turbid medium;

d) multi-gain amplification units for amplifying the detector signals for each source position-detection position pair, with each multi-gain amplification unit comprising means for setting a selected amplification factor.

The invention also relates to a medical image acquisition device comprising:

a) a measurement volume for accommodating the turbid medium;

b) a light source for irradiating the turbid medium from a plurality of source positions relative to the turbid medium;

c) a photodetector unit for acquisition of detector signals by detecting light emanating from the measurement volume from a plurality of detection positions as a result of said irradiation of the turbid medium;

d) multi-gain amplification units for amplifying the detector signals for each source position-detection position pair, with each multi-gain amplification unit comprising means for setting a selected amplification factor.

An embodiment of a method and device of this kind is known from U.S. Pat. No. 6,339,216 B1. The known method and device can be used for imaging an interior of a turbid medium, such as biological tissues. The method and device may be used in medical diagnostics for imaging an interior of a female breast. A turbid medium, such as a breast, is accommodated inside the measurement volume and irradiated with light from the light source. Light emanating from the measurement volume is detected in a number of detection positions for each source position and is used to derive an image of the interior of the turbid medium. The intensity of the light emanating from the measurement volume in different positions, and hence the intensity of the signals detected in those positions, may be spread over a wide dynamic range covering orders of magnitude. Therefore, each detector signal is channeled through a multi-gain amplifier unit to amplify the signal to an adequate level. The gain setting is determined by the intensity of the detected signal. Detected signals are recorded over a predetermined period of time inside a photodetector unit. The measurement volume may be bounded by a holder having only one open side, said open side being bounded by an edge portion. This edge portion may be provided with an elastically deformable sealing ring. Such a holder is known from U.S. Pat. No. 6,480,281 B1. Inside the measurement volume the turbid medium may be surrounded by a matching medium. This matching medium is used to counteract boundary effects stemming from the optical coupling of the turbid medium with its surroundings and to prevent optical short-circuits inside the measurement volume. An optical short-circuit occurs if light is detected that has not been sufficiently scattered and attenuated inside the measurement volume but outside the turbid medium. In that case the intensity of the insufficiently scattered and attenuated detected light may dwarf the intensity of detected light that has been scattered and attenuated through passage through the turbid medium. If a matching medium is used, a reference measurement is performed without the turbid medium being present.

It is a drawback of the known method and device that the procedure of determining the correct setting of a multi-gain amplifier unit, switching the multi-gain amplifier unit to the determined setting, and waiting for transient signals resulting from switching of the multi-gain amplifier unit to decay sufficiently results in a considerable amount of idle time during which no measurements can be performed.

It is an object of the invention to adapt the method and device so as to reduce the amount of idle time resulting from determining the correct setting of a multi-gain amplifier unit, switching the multi-gain amplifier unit to the determined setting, and waiting for transient signals resulting from switching the multi-gain amplifier unit to decay sufficiently. According to the invention, this object is realized in that the amplification factor for at least one source position-detection position pair is selected on the basis of an estimate of expected electrical signal strength. The invention is based on the recognition that basing the selection of the amplification factor on an estimate of expected electrical signal strength instead of on detected signal strength renders it possible to switch a multi-gain amplification unit and to wait for a transient signal resulting from said switching to decay sufficiently before an actual measurement is performed. A synchronization of the switching of a multi-gain amplification unit with the switching of one source position to another source position for irradiating the turbid medium results in a reduction of the total time it takes to image an interior of the turbid medium. As a consequence, the idle time involved in the procedure of determining the correct setting of a multi-gain amplification unit, switching the multi-gain amplification unit to the determined setting, and waiting for transient signals resulting from switching the multi-gain amplification unit to decay sufficiently is reduced. The amount of time saved increases as the number of source positions for which the amplification factors are selected on the basis of an estimate of expected electrical signal strength increases. The number of detection positions need not play a role here as for each source position the multi-gain amplification units may be switched simultaneously. The invention can reduce the time it takes to image an interior of a turbid medium by a factor of four to eight. If the estimated amplification factor for a single detector position is the same for two consecutive source positions, the multi-gain amplification unit need not be switched.

It is an additional advantage of the invention that the reduction of the time it takes to image an interior of a turbid medium provides a patient with more comfort in medical diagnostics, where the method and device may be used to image an interior of a female breast.

It is a further additional advantage of the invention that the reduction of the time it takes to image an interior of a turbid medium in medical diagnostics results in a reduction of image artifacts caused by a patient's movement.

It is a further additional advantage of the invention that the reduction of the time it takes to image an interior of a turbid medium in medical diagnostics allows more patients to be examined during a certain amount of time.

It is a further additional advantage of the invention that the reduction of the time it takes to image an interior of a turbid medium can be used to allow longer data gathering times, resulting in better signal-to-noise ratios. The better signal-to-noise ratios result from the fact that signals can be recorded over longer periods of time in the photodetector unit without making measurement times longer than in the prior art.

It is a further additional advantage of the invention that the selection of an amplification factor of a multi-gain amplification unit prior to a measurement reduces the effect of ill-defined transient signals, resulting in better measurement signals. If the estimated amplification factor for a single detector position is the same for two consecutive source positions, as discussed above, the multi-gain amplification unit need not be switched. Hence, a transient signal in such a multi-gain amplification unit that is not switched has a longer time to decay.

An embodiment of the method according to the invention is characterized in that the estimate of expected electrical signal strength is based on an analytical expression for the intensity of diffuse light in an infinite medium with a single source of light. In an infinite medium, the intensity of diffuse light is proportional to $e^{-kr}/r$. In this expression k represents the attenuation constant of the turbid medium and r represents the distance to the source position. This embodiment has the advantage of being easy to implement.

A further embodiment of the method according to the invention is characterized in that the estimate of expected electrical signal strength is based on a measurement of signal strength for a single source position and all detection positions. Based on symmetry arguments, which may depend on, for example, the shape of the turbid medium and the shape of the measurement volume, the amplification factor of all other source position-detection position pairs can be obtained. This embodiment has the advantage of being easy to implement, of being based on actually measured data, and of not requiring sophisticated calculations. Sophisticated calculations are not required as the amplification factor for all other source position-detection position pairs can be derived from relatively simple symmetry arguments.

A further embodiment of the method according to the invention is characterized in that the estimate of expected electrical signal strength is based on a measurement of signal strength for at least two neighboring source positions and all detection positions and extrapolating the difference between the selected amplification factors corresponding to the neighboring source positions. This embodiment has the advantage of being easy to implement, of being based on actually measured data, of not requiring sophisticated calculations, and of being applicable in measurement situations that have limited symmetry. If, for example, a measurement situation is such that it only has cylindrical symmetry, two or more measurements of signal strength may be performed for source positions lying in different locations with respect to the axis of symmetry, after which the amplification factors for all other source position-detection position pairs may again be obtained from symmetry arguments.

A further embodiment of the method according to the invention is characterized in that the estimate of expected electrical signal strength is based on historical data relating to a selection of an amplification factor of at least one multi-gain amplification unit. In medical diagnostics, where the method may be used for imaging an interior of a female breast, historical data may comprise the settings of the multi-gain amplifier units from a previous examination. This embodiment has the advantage that no calculations or measurements of signal strength are required and that the information needed to select the amplification factors for the various multi-gain amplification units already exists.

A further embodiment of the method according to the invention is characterized in that a matching medium surrounds the turbid medium inside the measurement volume, and in that the estimate of expected electrical signal strength is based on a radiation transport model of the matching medium and an estimate of the turbid medium. This embodiment has the advantage that it is capable of taking into account the presence of the turbid medium, a matching medium, and of any boundaries delimiting the measurement volume, without requiring an actual measurement of signal strength. As the estimate of expected electrical signal strength is made prior to an actual measurement, an estimate of the turbid medium is used in the radiation transport model.

A further embodiment of the method according to the invention is characterized in that a matching medium surrounds the turbid medium inside the measurement volume, and in that the estimate of expected electrical signal strength is based on the amplification factors selected during a reference measurement involving the matching medium. This embodiment has the advantage that it does not require complex calculations or the presence of a turbid medium. In medical diagnostics, where the method and device can be used to image an interior of a female breast, the latter means that a patient does not need to be present in order to select the amplification factors prior to the patient's examination.

A further embodiment of the method according to the invention is characterized in that the estimate of signal strength is based on characteristics relating to the turbid medium. In medical diagnostics, where the method and device can be used for imaging an interior of a female breast, predetermined characteristics relating to the turbid medium may comprise, for example, a patient's age, breast size, body mass index, etc. This embodiment has the advantage that no calculations or measurements of signal strength are required and that the information needed to select the amplification factors for the various multi-gain amplification units already exists.

According to the invention the device for imaging an interior of a turbid medium is adapted such that for at least one source position-detection position pair the means for setting a selected amplification factor are arranged for selecting the amplification factor on the basis of an estimate of expected electrical signal strength according to the method or any of the embodiment of the method according to the invention:

According to the invention, the medical image acquisition device is adapted such that for at least one source position-detection position pair the means for setting a selected amplification factor are arranged for selecting the amplification effect on the basis of an estimate of expected electrical signal strength according to the method or any of the embodiment of the method according to the invention. If, for example, the device is used to image an interior of a female breast, as is done in medical diagnostics, the device would benefit from any of the previous embodiments.

These and other aspects of the invention will be further elucidated and described with reference to the drawings, in which:

FIG. 1 schematically shows an embodiment of a device for imaging an interior of a turbid medium.

FIG. 2 schematically shows an embodiment of an electronic circuit for a multi-gain amplifier circuit.

Figure 1:
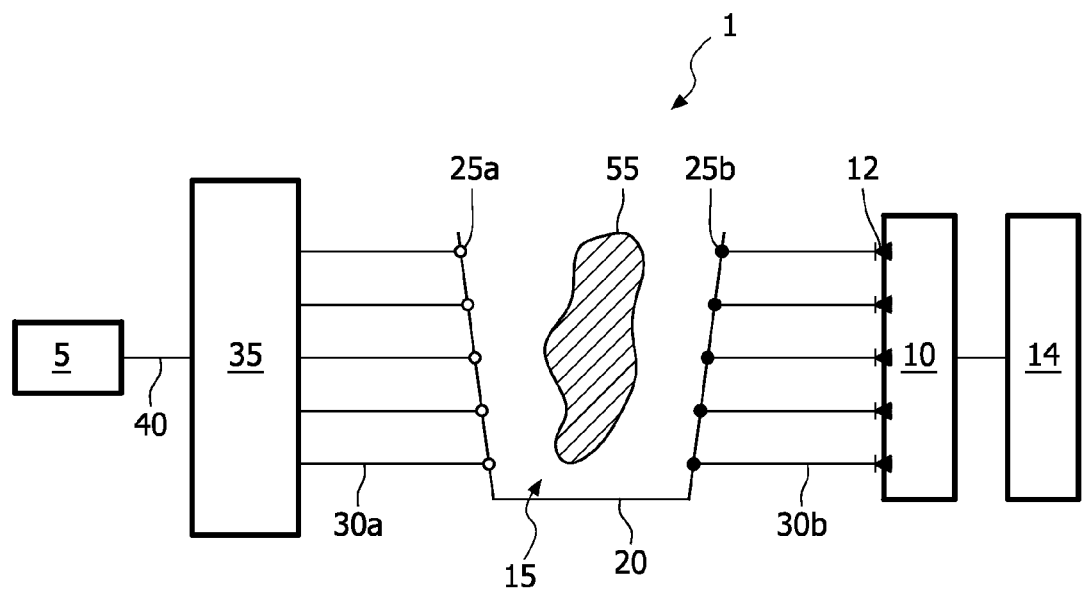

FIG. 1 schematically shows an embodiment of a device for imaging an interior of a turbid medium as known from prior art. The device 1 includes a light source 5, such as a laser, a photodetector unit 10, an image reconstruction unit 14 for reconstructing an image of an interior of the turbid medium 55 based on light detected using photodetector unit 10, a measurement volume 15 bounded by a receptacle 20, said receptacle 20 comprising a plurality of entrance positions for light 25a and a plurality exit positions for light 25b, and light guides 30a and 30b coupled to said entrance and exit positions. The device 1 further includes a selection unit 35 for coupling the light source 5 to a number of selected entrance positions for light 25a in the receptacle 20. The light source 5 is coupled to the selection unit 35 using input light guides 40. For the sake of clarity, entrance positions for light 25a and exit positions for light 25b have been positioned at opposite sides of the receptacle 20. In reality, however, both types of positions may be distributed around the measurement volume 15. A turbid medium 55 is accommodated in the measurement volume 15. The turbid medium 55 is irradiated with light from the light source 5 from a plurality of positions in that the selection unit 35 couples the light source 5 to successively selected entrance positions for light 25a. Light emanating from the measurement volume 15 is detected from a plurality of positions by means of the exit positions for light 25b and the photodetector unit 10. Photodiodes 12 may be used as detectors. The detected light is then used to derive an image of an interior of the turbid medium 55. This reconstruction process, which is based on, for example, an algebraic reconstruction technique or a finite element method, finds the most likely solution to the inverse problem, that is reconstructing an image that correctly fits the detected light.

Figure 2:
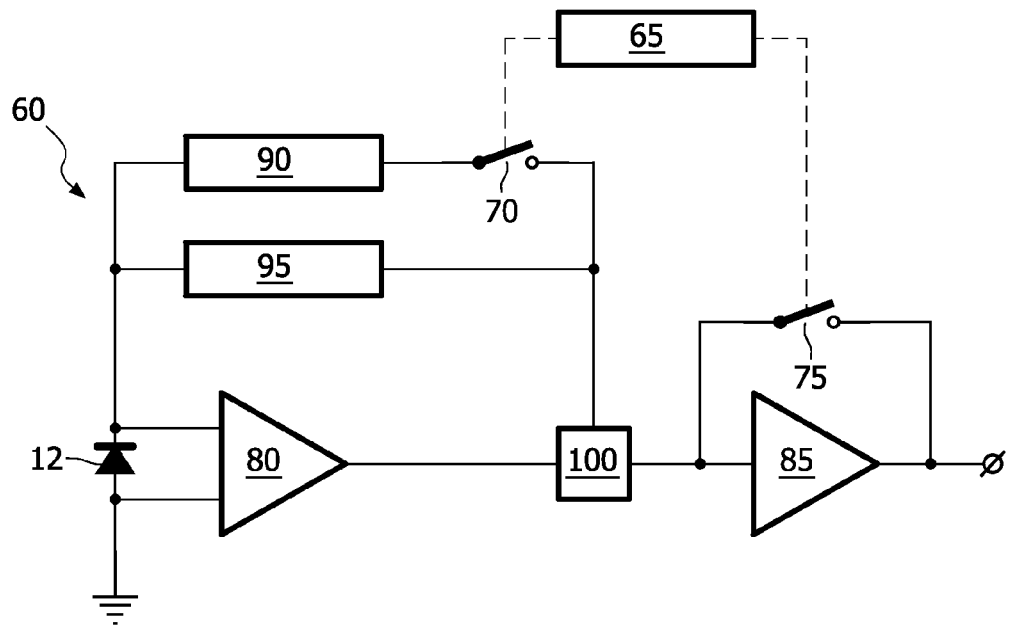

FIG. 2 schematically shows an embodiment of an electronic circuit for a multi-gain amplifier circuit 60. Such a circuit may be part of a multi-gain amplifier unit that, in addition to the amplifier circuit 60, may also contain means 65 for setting a selected amplification factor, such as a relay. The electronic circuit shown comprises a photodiode detector 12, two gain switches 70 and 75, two operational amplifiers 80 and 85, two resistors 90 and 95, and a filter 100 for reducing signal noise. Typically, the resistance of resistor 90 is lower by a few orders of magnitude than that of resistor 95. In the prior art, the gain of the amplifier circuit is first set to a low value for every detection position. The reason for this is that the output of the operational amplifier 80 should not be clipped to its maximum value, because this would cause unwanted heating effects. Then, depending on the measured signal strength, the gain is switched to a higher value, and so on. Switches 70 and 75 may be used for this. Especially the switching of switch 70 takes much time because it results in a transient signal that takes at least 250 ms to decay to a sufficiently low level before a measurement can start.

Figure 3:
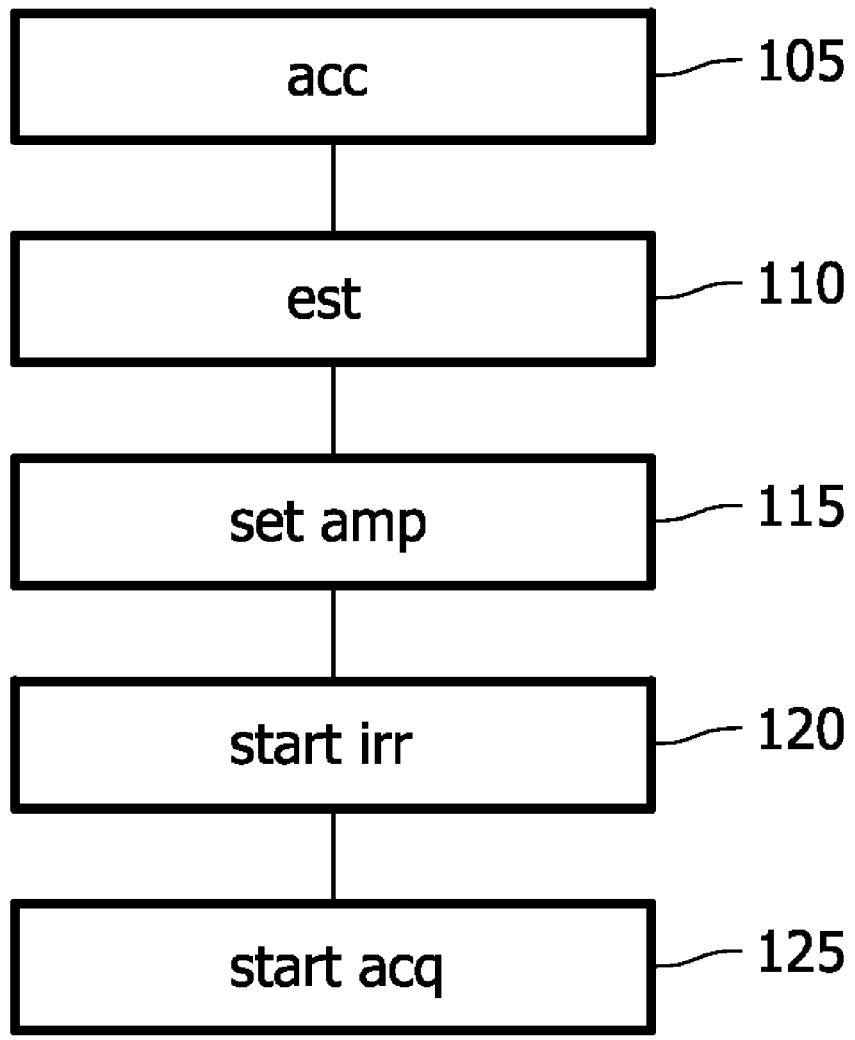
FIG. 3 is a flowchart illustrating the adapted method.

FIG. 3 is a flowchart illustrating the adapted method. Step 105 comprises accommodating the turbid medium 55 inside a measurement volume 15. Step 110 comprises estimating the expected electronic signal strength for at least one source position-detection position pair and selecting the amplification factor of the corresponding multi-gain amplification unit. The estimate may be based on, for example:

- An analytical expression for the intensity of diffuse light in an infinite medium with a single source of light. In an infinite medium, the intensity of diffuse light is proportional to $e^{-kr}/r$. In this expression k represents the attenuation constant of the turbid medium and r represents the distance to the source position.
- A measurement of signal strength for a single source position 25a and all detection positions 25b. Based on symmetry arguments, which may depend on, for example, the shape of the turbid medium and the shape of the measurement volume, the amplification factor of all other source position-detection position pairs can be obtained. If, for example, the turbid medium and the measurement volume have a cylindrical symmetry and the amplification factors for all detection positions are known following a measurement for one source position, the amplification factors for all detection positions and any other source position follow from a rotation of the amplification factor settings with the source position along the detector positions.
- A measurement of signal strength for at least two neighboring source positions 25a and all detection positions 25b and extrapolation of the difference between the selected amplification factors corresponding to the neighboring source positions 25a.
- Historical data relating to the selection of an amplification factor of at least one multi-gain amplification unit. In medical diagnostics, where the method may be used for imaging an interior of a female breast, historical data may comprise settings of the multi-gain amplifier units from a previous examination.
- A radiation transport model of the matching medium and an estimate of the turbid medium 55. This approach is similar to the first one, which uses an analytical expression for the intensity of diffuse light in an infinite medium with a single source of light, in that a model is used to predict the signal strength and a detector position. However, it has the advantage that it is capable of taking into account the presence of the turbid medium, of a matching medium, and of any boundaries bounding the measurement volume, without requiring an actual measurement of signal strength. The analytical expression for the intensity of diffuse light in an infinite medium with a single source of light does not take these matters into account.
- The selected amplification factors during a reference measurement involving the matching medium. This is a viable option if the matching medium matches the optical characteristics of the turbid medium to be imaged.
- Predetermined characteristics relating to the turbid medium 55. In medical diagnostics, where the method can be used for imaging an interior of a female breast, predetermined characteristics relating to the turbid medium may comprise, for example, a patient's age, breast size, body mass index, etc.

Step 115 comprises the setting of the amplification factor for the detector signal for each source position-detection position pair. Step 120 comprises starting irradiating the turbid medium 55 with light from a light source 5 from a plurality of source positions 25a relative to the turbid medium 55. Step 125 comprises the acquisition of detector signals by detection of light emanating from the measurement volume as a result of the irradiation of the turbid medium 55 from a plurality of detection positions 25b.

Figure 4:
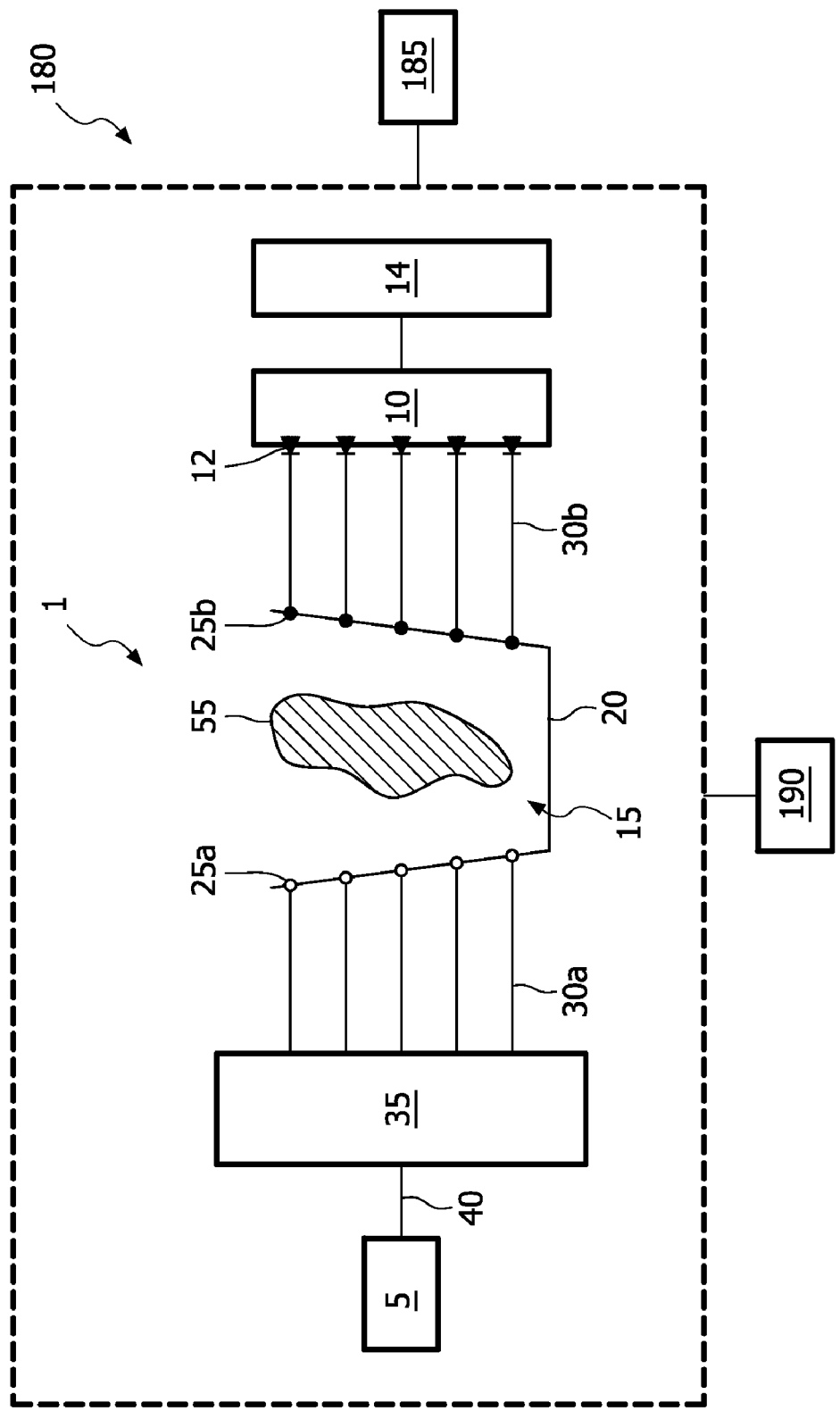
FIG. 4 shows an embodiment of a medical image acquisition device according to the invention.

FIG. 4 shows embodiment of a medical image acquisition device according to the invention. The medical image acquisition device 180 comprises the device 1 discussed in FIG. 1 as indicated by the dashed square. In addition to the device 1 the medical image acquisition device 180 further comprises a screen 185 for displaying an image of an interior of the turbid medium 45 and an input interface 190, for instance, a keyboard enabling and operated to interact with the medical image acquisition device 180.

It should be noted that the above embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. In the system claims enumerating several means, several of these means can be embodied by one and the same item of computer readable software or hardware. The mere fact that certain measures are recited in mutually different dependent claims does not indicate that a combination of these measures cannot be used to advantage.

The invention claimed is:

1. A method of imaging an interior of a turbid medium, comprising:
   a) accommodating the turbid medium inside a measurement volume;
   b) irradiating the turbid medium with light from a light source from a plurality of source positions relative to the turbid medium;
   c) acquiring detector signals by detection of light issuing from the measurement volume from a plurality of detection positions as a result of said irradiating of the turbid medium;
   d) amplifying the detector signals for each source position detection position pair using multi-gain amplification units, with each unit being set to a selected amplification factor,
   wherein the amplification factor for at least one source position detection position pair is selected on the basis of an estimate of expected electrical signal strength.

2. A method as claimed in claim 1, wherein the estimate of expected electrical signal strength is based on an analytical expression for the intensity of diffuse light in an infinite medium with a single source of light.

3. A method as claimed in claim 1, wherein the estimate of expected electrical signal strength is based on a measurement of signal strength for a single source position and all detection positions.

4. A method as claimed in claim 1, wherein the estimate of expected electrical signal strength is based on a measurement of signal strength for at least two neighboring source positions and all detection positions and extrapolating the difference between the selected amplification factors corresponding to the neighboring source positions.

5. A method as claimed in claim 1, wherein the estimate of expected electrical signal strength is based on historical data relating to a selection of an amplification factor of at least one multi-gain amplification unit.

6. A method as claimed in claim 1, wherein a matching medium surrounds the turbid medium inside the measurement volume, and wherein the estimate of expected electrical signal strength is based on a radiation transport model of the matching medium and an estimate of the turbid medium.

7. A method as claimed in claim 1, wherein a matching medium surrounds the turbid medium inside the measurement volume, and wherein the estimate of expected electrical signal strength is based on the amplification factors selected during a reference measurement involving the matching medium.

8. A method as claimed in claim 1, wherein the estimate of signal strength is based on predetermined characteristics relating to the turbid medium.

9. A device for imaging an interior of a turbid medium comprising:
   a) a measurement volume for accommodating the turbid medium;
   b) a light source for irradiating the turbid medium from a plurality of source positions relative to the turbid medium;
   c) a photodetector unit for acquisition of detector signals by detecting light issuing from the measurement volume from a plurality of detection positions as a result of said irradiation of the turbid medium; and
   d) multi-gain amplification units for amplifying the detector signals for each source position detection position pair, with each multi-gain amplification unit comprising means for setting a selected amplification factor,
   wherein for at least one source position detection position pair, the means for setting a selected amplification factor are arranged for selecting the amplification factor on the basis of an estimate of expected electrical signal strength.

10. A medical image acquisition device comprising:
    a) a measurement volume for accommodating a turbid medium including a biological tissue;
    b) a light source for irradiating the turbid medium from a plurality of source positions relative to the turbid medium;
    c) a photodetector unit for acquisition of detector signals by detecting light emanating from the measurement volume from a plurality of detection positions; and
    d) multi-gain amplification units for amplifying the detector signals for each source position-detection position pair, with each multi-gain amplification unit comprising means for setting a selected amplification factor,
    wherein for at least one source position detection position pair the means for setting a selected amplification factor are arranged for selecting the amplification factor on the basis of an estimate of expected electrical signal strength according to claim 1.

11. The device of claim 9, wherein each multi-gain amplification unit comprises:
    a first operational amplifier configured to receive the detector signal;
    a second operational amplifier configured to output the amplified detector signal; and
    a filter coupling an output of the first operational amplifier to an input of the second operational amplifier,
    wherein the means for setting the selected amplification factor comprises a pair of switches for selecting feedback paths for the first and second operational amplifiers.

12. The device of claim 9, wherein the estimate of expected electrical signal strength is based on an analytical expression for the intensity of diffuse light in an infinite medium with a single source of light.

13. The device of claim 9, wherein the estimate of expected electrical signal strength is based on a measurement of signal strength for a single source position and all detection positions.

14. The device of claim 9, wherein the estimate of expected electrical signal strength is based on a measurement of signal strength for at least two neighboring source positions and all detection positions and extrapolating the difference between the selected amplification factors corresponding to the neighboring source positions.

15. The device of claim 9, wherein a matching medium surrounds the turbid medium inside the measurement volume, and wherein the estimate of expected electrical signal strength is based on a radiation transport model of the matching medium and an estimate of the turbid medium.

16. The device of claim 10, wherein each multi-gain amplification unit comprises:
   a first operational amplifier configured to receive the detector signal;
   a second operational amplifier configured to output the amplified detector signal; and
   a filter coupling an output of the first operational amplifier to an input of the second operational amplifier,
   wherein the means for setting the selected amplification factor comprises a pair of switches for selecting feedback paths for the first and second operational amplifiers.

17. The device of claim 10, wherein the estimate of expected electrical signal strength is based on an analytical expression for the intensity of diffuse light in an infinite medium with a single source of light.

18. The device of claim 10, wherein the estimate of expected electrical signal strength is based on a measurement of signal strength for a single source position and all detection positions.

19. The device of claim 10, wherein the estimate of expected electrical signal strength is based on a measurement of signal strength for at least two neighboring source positions and all detection positions and extrapolating the difference between the selected amplification factors corresponding to the neighboring source positions.

20. The device of claim 10, wherein a matching medium surrounds the turbid medium inside the measurement volume, and wherein the estimate of expected electrical signal strength is based on a radiation transport model of the matching medium and an estimate of the turbid medium.

* * * * *